United States Patent [19]

Fischell et al.

[11] Patent Number: 4,573,994
[45] Date of Patent: Mar. 4, 1986

[54] REFILLABLE MEDICATION INFUSION APPARATUS

[75] Inventors: Robert E. Fischell, Silver Spring, Md.; Peter C. Lord, Valencina, Calif.

[73] Assignee: The Johns Hopkins University, Baltimore, Md.

[21] Appl. No.: 327,818

[22] Filed: Dec. 7, 1981

Related U.S. Application Data

[63] Continuation-in-part of Ser. No. 34,155, Apr. 27, 1979, Pat. No. 4,373,527.

[51] Int. Cl.⁴ ............................................... A61M 7/00
[52] U.S. Cl. ...................................... 604/891; 604/48; 604/140
[58] Field of Search ........................ 128/DIG. 12, 13; 604/27, 30, 31, 50, 65–67, 86, 131, 140, 147, 148, 175, 245, 411, 414

[56] References Cited

U.S. PATENT DOCUMENTS

| | | | |
|---|---|---|---|
| 3,578,037 | 5/1971 | Flynn | 604/51 X |
| 3,731,669 | 5/1973 | Fitzgerald | 604/51 X |
| 3,894,538 | 7/1975 | Richter | 604/891 |
| 3,935,876 | 2/1976 | Massie et al. | 128/DIG. 13 X |
| 3,951,147 | 4/1976 | Tucker et al. | 604/891 |
| 4,010,749 | 3/1977 | Shaw | 604/50 |
| 4,079,736 | 3/1978 | Lundquist | 604/52 |
| 4,146,029 | 3/1979 | Ellinwood | 604/891 |
| 4,308,866 | 1/1982 | Jelliffe et al. | 604/31 |
| 4,332,246 | 6/1982 | Thomson | 604/52 X |
| 4,373,527 | 2/1983 | Fischell | 128/DIG. 13 |

Primary Examiner—Henry J. Recla
Assistant Examiner—Francis J. Jaworski
Attorney, Agent, or Firm—Robert E. Archibald; Howard W. Califano

[57] ABSTRACT

Apparatus and method for filling, or refilling, the internal reservoir of a medication infusion system, wherein filling or refilling is permitted only when a means for injecting medication is properly positioned relative to the reservoir. Prior to filling or refilling, a pressure integrity check can be made to help assure that injected medication enters the reservoir without leakage. Additionally, flushing of a portion or all of the medication reservoir can be accomplished if desired. Medication is introduced to and is stored in the reservoir at a pressure below ambient body pressure.

64 Claims, 7 Drawing Figures

REFILLABLE MEDICATION INFUSION APPARATUS

CROSS-REFERENCE TO RELATED APPLICATION

This is a continuation-in-part of a patent application, Ser. No. 34,155, filed on Apr. 27, 1979 and now U.S. Pat. No. 4,373,527.

BACKGROUND AND/OR ENVIRONMENT OF THE INVENTION

1. FIELD OF THE INVENTION

The present invention pertains generally to the filling of implanted infusion apparatuses, and more particularly to an implantable infusion apparatus, an apparatus for filling the infusion apparatus, and a method for accomplishing such filling.

2. DESCRIPTION OF THE CONTEMPORARY AND/OR PRIOR ART

The desirability of being able to implant a medication infusion pump in a human or animal body has been recognized by prior and contemporary technology. Patents such as U.S. Pat. No. 4,077,405, U.S. Pat. No. 4,033,479, and U.S. Pat. No. 4,073,292 recognize the desirability of dispensing medication from within the body. Where medication can be dispensed or infused directly to that portion of the body at which the medication is to be applied, lower concentrations of the medication and diminished side effects can be realized.

To achieve longer life for such implantable infusion apparatuses as well as for infusion apparatuses maintained external to the body, a feature of refillability has been suggested by both the prior and contemporary art. Summers, in U.S. Pat. No. 3,527,220, discloses a pump for administering drug to a body wherein the pump has a "self-sealing" port through which the pump can be filled with an appropriate drug. Similarly, Tucker et al and others in U.S. Pat. Nos. 3,951,147 and 4,193,397 discuss the periodic refilling of an infusate pump by injecting drug through an inlet septum into a storage chamber implanted beneath the skin. Likewise, Ellinwood, in U.S. Pat. Nos. 3,692,027, 3,923,060, 4,003,379, and 4,146,029, discloses a cylindrical inlet through which medication in a dispensing apparatus can be replenished. Similarly, Blackshear, in U.S. Pat. No. 3,731,681, discloses an inlet which is closed by means of a self-puncture sealing refill stopper. An invention of Blackshear (U.S. Pat. No. 3,731,681) shows another infusion pump wherein drug is fed through a self-sealing plug into an infusate chamber. Such prior and current apparatuses generally disclose the use of a resealable, or self-sealing, septum through which a drug refilling hypodermic needle can pass.

Another implanted device for supplying medicines is disclosed in U.S. Pat. No. 3,894,538 which provides for refillability through spring valves.

Those working with implant technology have also recognized the problem of bacteria flowing from a medication infusion pump into the body. Tucker, in U.S. Pat. No. 3,951,147, addresses this problem by first sterilizing the pump taught therein before implantation and by providing an outlet filter intended to trap air bubbles and debris.

Another problem heretofore unsolved by the prior art is associated with the necessity to refill a medication reservoir under pressure. If the portion of the refilling apparatus which enters the reservoir is not properly placed, a potentially fatal dose of medication can be injected directly into the patient in which the device is implanted.

These various inventions have underscored the benefit and advantages of designing an implantable medication device to be refillable. However, the above-cited technology fails to disclose various features which might render such a refillable implantable device safer, more convenient, and improved in operation.

SUMMARY OF THE INVENTION

The present invention is directed to numerous features which render refillability of infusion apparatuses safer, more effective, and practical then taught by the prior art. For example, where medication of high concentrations are injected into an apparatus implanted in the body, it is important that the medication not be inadvertently injected into the body itself and that the injection needle employed to deliver the medication be properly placed prior to the injection of any medication. It is additionally desirable to preclude dispensing of medication into the body if the injection needle is withdrawn or otherwise displaced during the refilling process.

Accordingly, it is one object of the present invention to provide an implantable apparatus having a conically shaped inlet port having a relatively hard, smooth, or polished inner surface, the conically tapered inlet port being tapered from its maximum diameter to its minimum diameter where it terminates in a self-sealing septum. As a result, when a hypodermic needle is inserted through the skin of the body in which the infusion apparatus is implanted, the hypodermic needle, guided by the inlet port, can pass through the self-sealing septum and, thereafter enter a medication reservoir or an antechamber thereof with the needle stopping when it comes into contact with the floor or such other predetermined part of the reservoir or antechamber. The floor of the antechamber or other contacting surface is preferably of a material such as a soft metal which will not damage the point of the hypodermic needle which is constructed of a harder material.

In an antechamber configuration, the present invention teaches, extending to the surface of the implantable apparatus from the antechamber floor, a conducting element which ends at a contact surface. A second needle, fixed in position relative to the hypodermic needle and insulated therefrom, also passes through the skin stopping when it touches the contact surface. Proper insertion and positioning of the hypodermic needle during filling therefore can be determined by the forming of an electric circuit which includes a conduction path formed by the hypodermic needle, the soft metal floor of the antechamber, the conducting element, the contact surface thereof, and the second needle which comes in contact therewith. As an alternative, proper placement of the hypodermic needle can be determined by the use of a photoelectric detector means or by engagement of a mechanical valve. In the case of a mechanical valve, medication cannot be communicated to the reservoir unless the needle pushes a valve poppet, as a result of correct placement, and therefore opens a passage to the reservoir.

Further, to assist the proper initial alignment of the needle relative to the center line of the inlet port, needle guides are provided in a communication head or the like which is placed external to the body proximate to the implantable apparatus during filling.

In accordance with the present invention, an antechamber is placed between the inlet port of the apparatus where medication is supplied thereto and the reservoir chamber where medication to be dispensed is stored. The size of the antechamber is selected for each medication so that it is sufficiently small to preclude serious harm to a patient should medication inadvertantly leak out of the antechamber.

It is also an object of the present invention to prevent the growth of germs in the implantable pump by providing a bacteriacidal agent in the antechamber or reservoir chamber or both of the present invention. Combining the medication delivered by the pump with a bacteriacidal agent provides a preventive rather than curative solution as accomplished, for instance, by the use of an outlet filter as taught by the prior art. Additionally, the antechamber is in communication with the medication reservoir through a filter which precludes passage of bacteria from the antechamber to the medication reservoir.

To further avoid medication contamination, the hypodermic needle can be provided with a stylet which prevents skin, hair, and other debris from entering the opening or discharge port of the hypodermic needle as it pierces the skin. The stylet can be withdrawn when the hypodermic needle is in place.

Further, it is an object of the invention, when used in an implantable apparatus, to provide a safe method of filling the reservoir chamber thereof with medication. Filling of the present invention can occur only after the dictates of a plurality of safeguards have been complied with. In particular, no medication can be injected unless the hypodermic needle or syringe delivering the medication is properly positioned in the antechamber, as hereinbefore described. In one embodiment, the antechamber is initially filled with a baetericidal agent, saline, or other innocuous solution to check for pressure integrity by determining if there is any undesired leakage. The liquid is then withdrawn and a desired medication is then injected into the antechamber. By increasing the pressure under which the medication is injected, medication (such as insulin, heparin, or the like) enters the antechamber and then the medication reservoir chamber until it is filled, at which time a fill switch is activated. Once the medication reservoir chamber is filled, the antechamber is flushed again with a selected solution, some of which remains in the antechamber until the next filling. Another safety feature precludes medication refilling unless the proper medication is present for the particular patient.

An additional safety aspect of the present invention concerns, in one embodiment, the sucking of medication into the medication reservoir by negative pressure rather than filling by the pumping of medication therein. Since medication is not pumped, the possible catastrophic complications of improper refilling and the pumping of medication directly into the patient, rather than into the reservoir, is avoided.

While several features of the present invention relate specifically to implantable apparatuses, a few features of the invention also may have application in external medication infusion pumps. Although safe reliable refillability is particularly important where the apparatus is implanted, such benefits apply similarly to external pumps which may be differently configured as compared to the implantable variety. Specifically, verification of the medication to be injected and the use of a valve, mechanically opened by a refilling needle to permit access to the medication reservoir, may have application in an external device.

These objects, as well as other objects and advantages of the present invention will become radily apparent after reading the ensuing description of several non-limiting illustrative embodiments and viewing the accompanying drawings.

BRIEF DESCRIPTION OF THE DRAWINGS

In order that the present invention may be more fully understood it will now be described, by way of example, with reference to the accompanying drawings in which.

DESCRIPTION OF THE PREFERRED EMBODIMENTS

Figure 1:
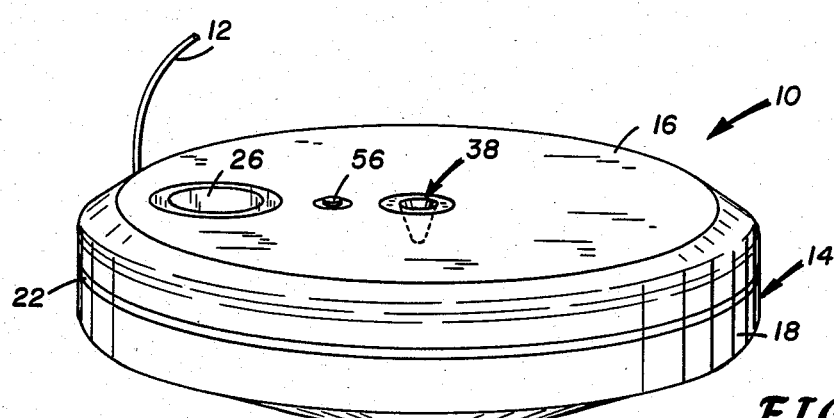
FIG. 1 is pictorial representation, in perspective, of an implantable medication infusion apparatus incorporating the principles of the present invention.
Figure 2:
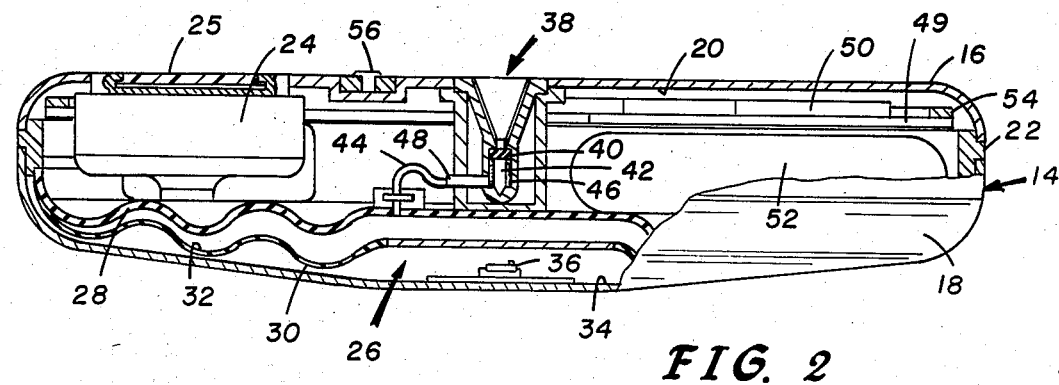
FIG. 2 is a partially broken away side view of the medication infusion apparatus of FIG. 1.

Referring now to the Figures, and more particularly to FIGS. 1 and 2 thereof, there is illustrated therein an implantable medication infusion pump (IPIP) 10. The IPIP 10 can be programmed to provide a controlled flow of medication, upon command, which is delivered through a catheter 12 into the body in which the IPIP 10 is implanted. The IPIP 10 includes a housing 14 having a cover portion 16 and a mating base portion 18 which form therebetween a chamber 20. The cover portion 16 and the base portion 18 are preferably constructed of titanium or another suitable biologically compatible material having the necessary characteristics required by the invention and are joined together at a seam 22 by welding or the like.

Disposed within the chamber 20 of the IPIP 10 is a fluid accumulator 24 which includes a pressure sensing membrane 25 that opens through the surface of the cover portion 16. The output of the accumulator 24 is sent to the catheter 12 through a flow restrictor (not shown). The input of the accumulator 24 comes from a pulsatile pump (not shown) that receives fluid from a medication reservoir 26. The medication reservoir 26 is disposed within the base portion 18 and is defined by a wall 28 and the bottom of the base portion 18. Disposed between the wall 28 and the bottom of the base portion 18 is a flexible diaphragm 30 which divides the medication reservoir into a medication chamber 32 and a vapor chamber 34. The medication chamber 32 is in communication with the pump and the vapor chamber 34 is filled with a saturated vapor and some liquid of a fluorocarbon such as Freon 113 or some other appropriate pressurant. Over normal body temperatures, Freon 113 has a linear pressure characteristic as it changes from liquid to vapor and visa versa and therefore, at the essential constant temperature of the human body, it will maiantain the vapor chamber 34 and therefore the medication chamber 32 at a fixed pressure regardless of the amount of medication disposed within the medication chamber 32. As the medication chamber 32 is filled with medication, as hereinafter described, the flexible diaphragm 30 distends downwardly (with reference to the Figure) toward the bottom of the base portion 18 and, eventually comes in contact with a limit switch 36 which senses that the medication chamber 32 has reached a preselected degree of fullness. A metallic or metal coated elastomer is used for the flexible diaphragm 30 to prevent diffusion of the pressurant from entering the medication chamber 32 and to prevent medication in the chamber 32 from entering the vapor chamber 34.

The medication chamber 32 is refilled, when depleted, through an inlet port 38 which opens through the surface of the cover portion 16. The inlet port 38 is sealed from the outside world by a self-sealing septum 40, preferably constructed of silicon rubber or another material which has the necessary self-sealing and longevity characteristics and which is also impervious to the actions of the fluid contained in an antechamber 42. The inlet port 38 is separated by the septum 40 from the antechamber 42 which is in communication with the medication chamber 32 through a conduit 44. An annular filter 46 is disposed within the antechamber 42 and all fluid communicated to the medication chamber 32 must pass through the filter 46. The filter 46, as well as the other antechamber filters which will be hereinafter described in conjunction with the other embodiments of the present invention, preferably has a pore size sufficiently small to preclude the passage of bacteria from the antechamber to the medication chamber. A pore size of 2 microns or less is considered appropriate. However, selection of the actual pore size is well within the skill of one of ordinary skill in the art once the size of the bacteria to be precluded is identified.

Disposed between the antechamber 42 and the medication chamber 32 in the conduit 44 is a one-way pressure activated valve 48. The valve 48, as further illustrated in FIG. 3, disposed in the conduit 44 is of the spring actuated ball poppet valve type and precludes flow through the conduit 44 until sufficient pressure builds up in the antechamber 42 to cause the ball to move to open the valve thus permitting flow into the medication chamber 32.

Figure 6:
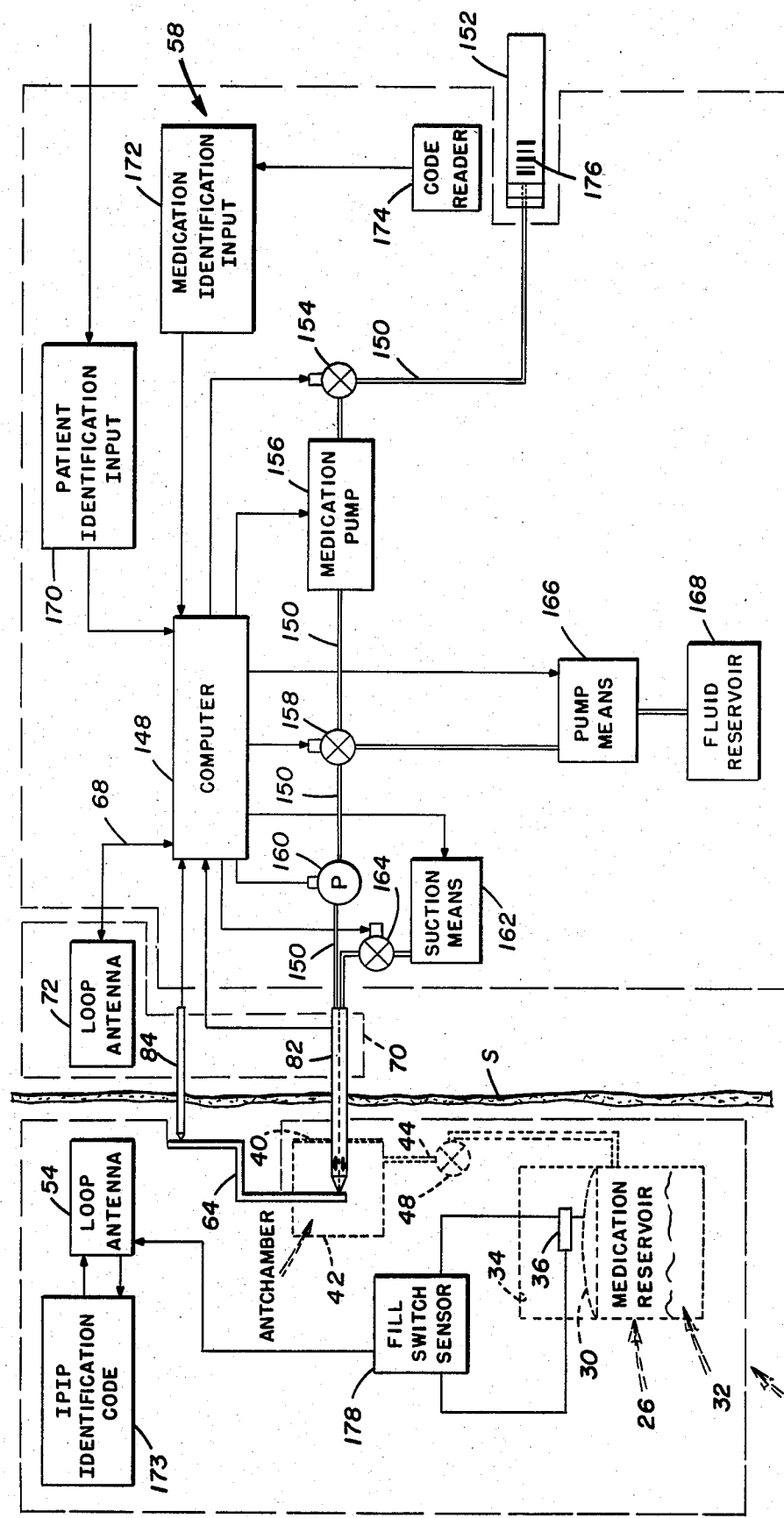
FIG. 6 is a block diagram of the control system employed in one embodiment of the present invention.

Also disposed within the chamber 20 of the IPIP 10 is an electronic control circuit board 49 having circuitry 50 disposed thereon and a battery 52 which powers the circuitry 50 and the pump. Disposed adjacent to the uppermost area of the cover portion 16 within the chamber 20 is a communications loop antenna 54. If the battery 52 is rechargeable, the loop antenna 54 is hooked to a recharging circuit and can be employed to receive, by inductive coupling, an AC signal emanating from a transmitting loop antenna hereinafter described. The loop antenna 54 is also employed to communicate various command instructions from an external programming device to the control circuits 50 and to send telemetry data out of the IPIP 10. Opening through the surface of the cover portion 16 is an alarm electrode 56 which is coupled to the circuitry 50 and provides an alarm signal to the patient in which the IPIP 10 is implanted as is preselected and programmed. The switch 36 is also coupled to the circuitry 50 and, when the switch 36 is actuated by distending of the flexible diaphragm 30, a signal is coupled to the loop antenna 54 and is transmitted therefrom for reception by a medication injection unit (MIU) 58, as illustrated in FIGS. 3 and 6.

Figure 4:
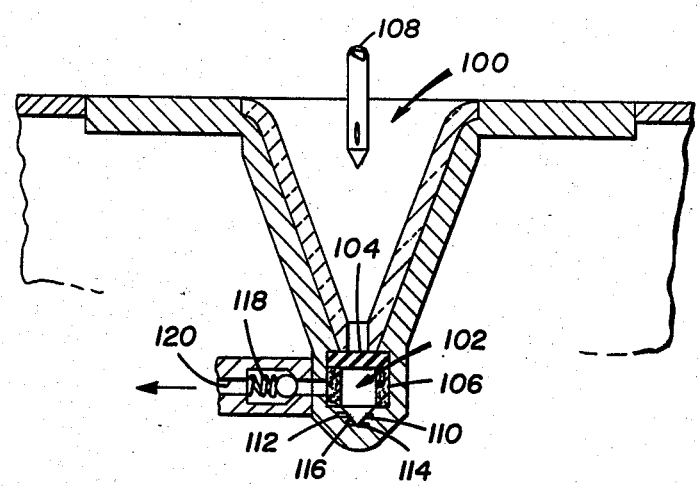
FIG. 4 is a partially broken away side view of an alternate embodiment of the present invention showing a hypodermic needle ready for positioning in the antechamber thereof and two alternate means for detecting the presence of the hypodermic needle in the antechamber.
Figure 3:
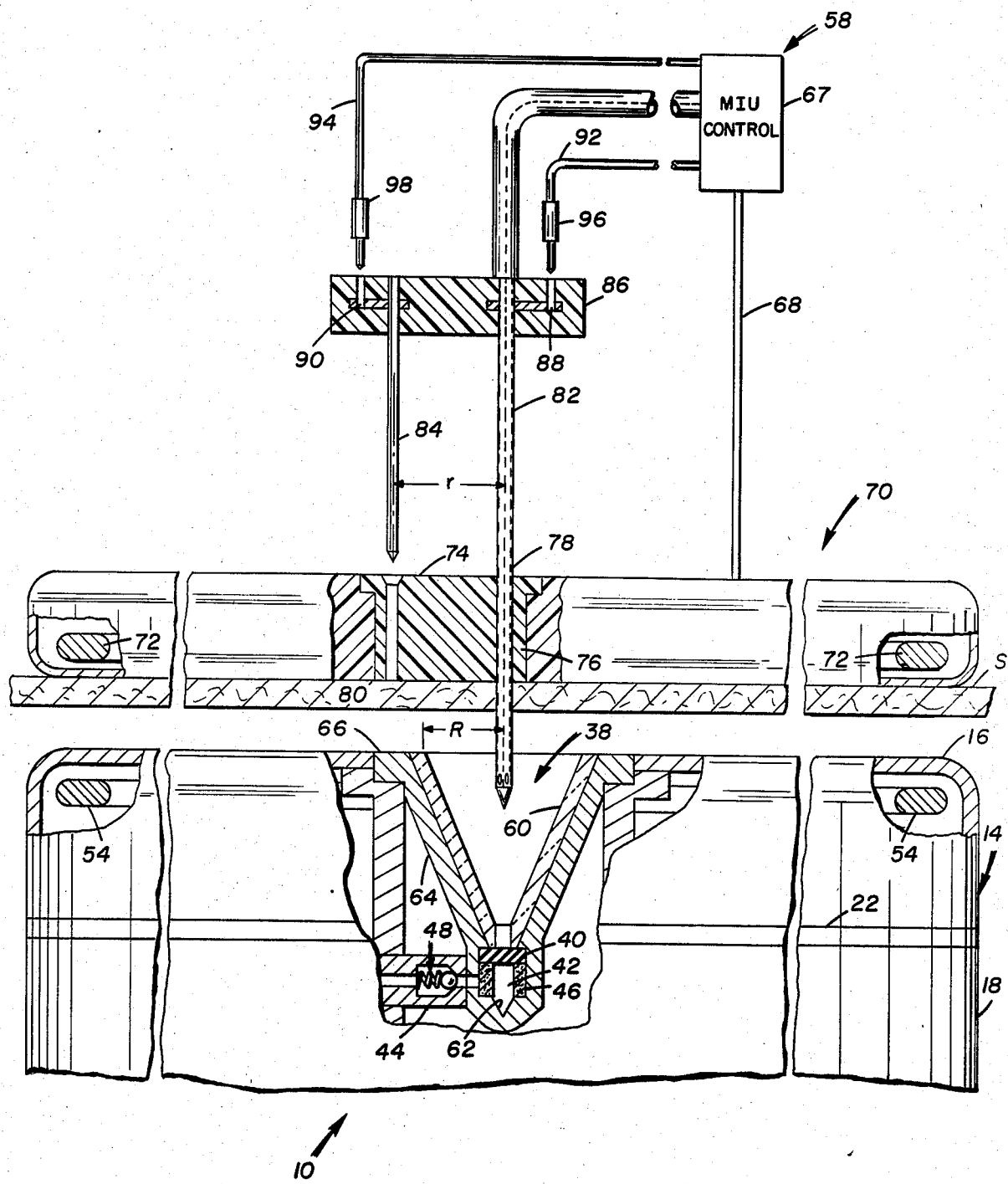
FIG. 3 is an enlarged fragmentary cross-sectional side view of an apparatus constructed in accordance with the priciple of the present invention showing certain elements concerned with filling the implantable refillable medication infusion pump thereof.

Referring now to FIG. 3, the manner in which the MIU 58 is used to fill the IPIP 10 can be seen. The IPIP 10 is implanted at a preselected location within the body of a patient with a desired orientation and at a desired depth below the skin S of the patient. This orients the inlet port 38 so that it is readily accessible by a hypodermic needle inserted through the skin S. The inlet port 38 has a generally conical or funnel shaped polished inner surface 60 which is relatively hard and smooth and which may be formed of glass, ceramic, or the like. The concial inlet port 38 can have a linearly varying diameter as illustrated in FIG. 3 or may include a flared bell or horn form as illustrated in FIG. 4. The greatest radius of the surface 60 is a distance R which is greater than the maximum distance an error in positioning might cause a hypodermic needle, which is to be directed down through the conical inlet port 38 and through the septum 40 into the antechamber 42, to deviate from the center of the antechamber 42. Therefore, once the parameters for the possible misalignment of a needle to be inserted are determined, the distance R is made slightly larger than such distance of error. When a hypodermic needle is then inserted it will be guided by the polished surface 60 down through the septum 40 so that it is in communication with the antechamber 42 without danger of entirely missing the inlet port 38. When a hypodermic needle pierces the self-sealing septum 40 and is inserted into the antechamber 42 it bottoms out on a surface 62 which forms the floor of the antechamber 42 and which is constructed of a relatively soft metal such as titanium such that the relatively hard tip of the needle will not be damaged upon contact therewith. The surface 62 is conductive and is coupled to a conductor 64 which terminates in an annulus 66 adjacent ot the outer surface of the cover portion 16. The annulus 66 can be electrically connected to the cover portion 16 as illustrated or may be isolated therefrom.

Figure 7:
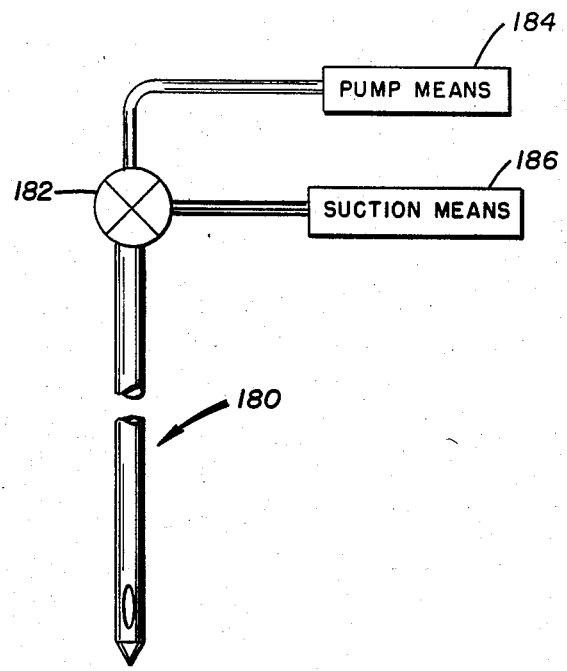
FIG. 7 is a pictorial representation of an alternate embodiment of the filling needle of the present invention.

The medication injection unit or MIU 58 accomplishes several control functions, the operations of which will be fully described in conjunction with FIG. 7. The control assembly 67 of the MIU 58 is coupled by a cable 68 to a communication head 70. The communication head 70 serves the dual function of permitting communication with the IPIP 10 and aiding in the alignment of the hypodermic needle which is to be inserted into the antechamber 42. The communication head 70 includes a loop antenna 72 which matches and is configured for communication with the loop antenna 54 disposed in the housing 14 of the IPIP 10. The loop antenna 72 is coupled to the cable 68 of the MIU control assembly 67. To assist in achieving proper alignment of the hypodermic needle to be inserted into the antechamber 42, the control head is constructed to be of a shape congruent to that of the housing 14 of the IPIP 10 to facilitate in the adjacent placement and alignment of these two structures. This is the case since it is well known that people have an excellent ability to align similar shapes. Alternately, the communication head 70 and the housing 14 of the IPIP 10 could be circular, eliptical, or even oblong and the communication head 70 and housing 14 of the IPIP 10 might have other enhancements to insure alignment such as a complementary concave and convex surface or otherwise mating or shaped surfaces or the like. Centrally disposed in the communication 70 is a needle guide 74 which is removable from an aperture 76 disposed in the communication head 70. The needle guide is preferably constructed of a sterilizable plastic and can be discarded and replaced after each use. Longitudinally disposed through the needle guide insert 74 is a pair of apertures 78 and 80 which are provided for accommodating therein, respectively, a hypodermic needle 82 and an electrode needle 84. The mouths of the apertures 78 and 80 are tapered to facilitate acceptance of the hypodermic needle 82 and the electrode needle 84. Although the communication head 70 incorporates several functions, it is to be understood that the alignment function thereof could be embodied in a control head structure whose sole function is to facilitate alignment. In such a case, a solid disc structure having a central aperture for guiding at least one needle or the like would be provided.

The hypodermic needle 82 and the electrode 84 are fixedly secured to a holder 86 which mounts these two elements in substantially parallel relationship at a distance r. The distance r between the hypodermic needle 82 and the electrode needle 84 is greater than the magnitude of R, the largest radius of the inlet port 38. Both the hypodermic needle 82 and the electrode needle 84 are electrically conductive and are coupled, respectively, to female connectors 88 and 90 mounted in the insulating holder 86. The connectors 88 and 90 can be engaged, respectively, by leads 92 and 94 which terminate respectively, in male connectors 96 and 98 adapted to mate, respectively, to the female connectors 88 and 90. The leads 92 and 94 are connected to the MIU control assembly 67 and sense whether or not there is electrical continuity between the hypodermic needle 82 and the electrode needle 84.

As the hypodermic needle 82 is lowered in through the inlet port 38 to the antechamber 42 the electrode 84 approaches the outer surface of the cover portion 16 or the annulus 66 depending upon whether or not the annulus has been electrically connected to the cover portion 16 or whether the annulus itself is sized to facilitate contact. In either case, when the hypodermic needle 82 touches the floor of the antechamber 42 at the surface 62 thereof, the electrode 84 is in electrical contact therewith through the conductor 64. Circuit continuity is thereby achieved between electrical leads 92 and 94 indicating that the hypodermic needle 82 is correctly positioned. When this circuit is thusly closed, this condition is detected by the MIU control assembly 67.

Alternate methods of determining that the hypodermic needle 82 has been correctly positioned are possible. Specifically, with reference to FIG. 4, there is illustrated therein an alternate inlet port 100. The inlet port 100 is substantially conically shaped except for a bell-type flare at the uppermost surface thereof and defines a path to an antechamber 102 covered by a septum 104. An annular filter 106 is disposed within the antechamber 102 and functions in the same manner as the filter 46 disposed within the antechamber 42 of FIG. 3. A ball valve 118 is disposed in a conduit 120 and serves the same function as the ball valve 48 and the conduit 44.

For economy of illustration, two alternative optical embodiments for determining the position of a hypodermic needle 108 are illustrated in antechamber 102 although either one or the other would be employed. An optical light source 110 focuses a light beam across the antechamber 102 to a light detector 112. When the hypodermic needle 108 enters the antechamber 102, the beam from the source 110 is interrupted. The interruption of this beam is employed to actuate a circuit or switch, not illustrated, which is in turn coupled back to the MIU control to indicate that proper needle placement has been achieved. Instead of employing light source 110 and detector 112, a beam from light source 114 can be reflected off the hypodermic needle 108 toward a light detector 116 when the hypodermic needle 108 is properly positioned. This reflection effect can also be similarly communicated electrically to an appropriate circuit or switch.

Figure 5:
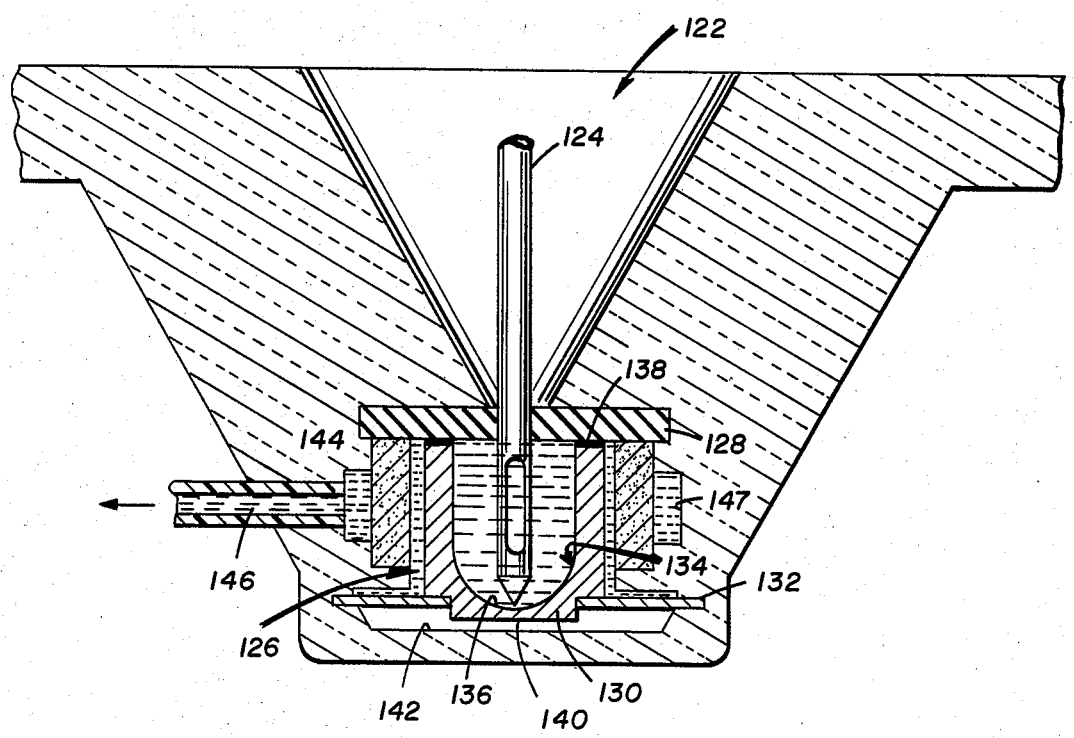
FIG. 5 an enlarged fragmentary cross sectional view of an alternate antechamber of the present invention.

Still another manner of determining proper placement of a means for injecting medication (such as a hypodermic needle) relative to an antechamber can be observed with reference to FIG. 5. FIG. 5 shows an inlet port 122 for guiding a needle 124 into an antechamber 126 through a septum 128. Disposed within the antechamber 126 is a valve poppet 130 reciprocally mounted by a flexible diaphragm 132 fixed secured to the walls of the antechamber 126. The valve poppet 132 forms therein a recess 134 which is dimensioned to accept therein the hypodermic needle 124. When the needle 124 contacts the bottom 136 of the recess 134, the valve poppet 130 then moves away from the septum 128 creating an opening between the septum 128 and a valve seat 138. Movement of the valve poppet 130 is limited by the distance between the outer lowermost surface 140 thereof and a surface 142 of the antechamber 126. When the valve seat 138 is open, the recess 134 is placed in communication with the balance of the antechamber 126 therefore permitting fluid introduced through the needle 124 to flow through a filter 144 into a conduit 146 through an annular fluid manifold 147. The conduit 146 is in communication with a medication reservoir, not illustrated. When the hypodermic needle 124 is withdrawn from the antechamber 126 the valve poppet 130 returns to its rest position thereby once again isolating the septum 128 from the medication reservoir, not illustrated, and therefore preventing any flow of medication out through a hole which may be in the septum 128.

It should be apparent to one skilled in the art that biasing means other than the resilient diaphragm 132, such as springs or the like, which either act in compression or in tension can be employed to properly move the poppet 130. In addition, the valve seat 138 can engage a fixed structure other than the septum 128.

Thusly, proper positioning of the hypodermic needle 124 causes opening of the valve poppet 130. The significance of this particular configuration is that it provides for very simple medication reservoir refilling including the ability to suck fluid out of the reservoir so as to change medication, to flush out old medication, or to sample the medication to determine if it still has the desired potency and to see if it has developed harmful bacteria. It is contemplated that the medication reservoir of the present invention would be at a negative pressure i.e. one less than ambient or atmospheric pressure and therefore, when a fluid is presented in the antechamber it will be sucked into the medication reservoir without pumping. If a vial of medication is fitted with a means for injecting medication (such as a hypodermic needle) and the needle is introduced into the antechamber 126, when the hypodermic needle pushes the valve poppet 130, medication within the vial will be sucked into the medication reservoir refilling the same. The term injection as used in this application defines a refilling action whether the fluid is either forced by positive pressure into the medication reservoir or drawn into the medication reservoir by maintaining the reservoir at a negative pressure, e.g., below ambient pressure. This sucking and refilling action cannot take place unless the needle 124 is properly positioned and therefore the aforedescribed structure acts as a unique guard mechanism to preclude inadvertent pumping of medication into a patient as a result of improper hypodermic needle placement. This is in contrast to the previously described embodiments of the present invention wherein it is contemplated that medication will be pumped in at a positive pressure and electrical mseans are provided for determining that the hypodermic needle employed is properly positioned.

The operation and control functions of the MIU 58 can be observed with reference to FIG. 6. The MIU 58 includes a computer 148 which is responsible for all of the control functions of the MIU 58. The computer 148 may be a microprocessor and include suitable memory dedicated just for use in the MIU or may form a part of a programming unit used to program the control functions of the IPIP 10. The computer 148 is coupled to the coil 72 for communication directed to the coil 54 disposed within the IPIP 10. Also connected to the computer 148 are electrode needle 84 and hypodermic needle 82 such that the electrical continuity between these two probes can be determined by the computer using additional circuitry (not shown) as may be necessary.

Medication is supplied to the hypodermic needle 82 by the MIU 58 through a path of conduit 150 which begins at a medication vial 152 and terminates with the hypodermic needle 82. Disposed between the medication vial 152 and the hypodermic needle 82 is a valve 154, a medication pump 156, a valve 158, and a pressure transducer 160. The hypodermic needle 82 is of the dual lumen type and one of the lumens thereof is in communication with the conduit 150, the other lumen thereof being in communication with a suction means 162 through a valve 164. The valve 158 in addition to permitting communication through the conduit 150, in one position thereof, is also in communication, in the other position thereof, with a pump means 166 which is in turn in communication with a fluid reservoir 168. The operation of the valve 154, the medication pump 156, the valve 158, the suction means 162, the valve 164, and the pump means 166 are all controlled by the computer 148.

Electrically coupled to the computer 148 is a patient identification input 170 and a medication identification input 172. Coupled to the medication input 172 is a code reader 174 for reading a bar code 176 or the like disposed on the medication vial 152.

With reference to FIGS. 2, 3, and 6, the manner in which the medication reservoir 26 is filled can be observed. This procedure is particularly safe because of the redundant safety features incorporated and because various alternatives of procedure are provided for to suit specific needs. Initially, to initiate filling, the communications head 70 is aligned with the IPIP 10 implanted within the patient under the skin S. A sterile needle guide 74 would then be placed within the aperture 76 of the head 70 and the hypodermic needle 82 and the electrode needle 84 would then be placed through the apertures in the needle guide insert 74 piercing the skin S such that the electrode needle 84 would contact the outer surface of the cover portion 16 and the needle 82 would contact the floor surface 62 of the antechamber 38. Continuity between the hypodermic needle 82 and the electrode needle 84 would therefore result from contact through conductor 64 and this would be sensed by the computer 148. If the embodiments of FIG. 4 were employed, just a hypodermic needle and not an electrode needle would be inserted with the optical system detecting proper needle placement. No other function of the computer 148 controlling the medication pump 156, the suction means 164 the pump means 166 could take place absent sensed continuity between hypodermic needle 82 and electrode needle 84 or proper needle placement as determined optically.

Either before proper needle placement is established or shortly thereafter, the medication vial 152 would be inserted in the MIU in a manner so that it was in communication with the conduit 150. For instance the MIU might have a piercing needle which is inserted through a septum disposed at the top of the medication vial. As this is accomplished, the code reader 174 would read the bar code 176 on the vial 152 in a conventional manner and, through the medication identification input 172, tell the computer what medication has been positioned for use. A patient identification input 170, either previously entered into the computer or inputted into the computer through the use of an identifying code on a patient ID bracelet, a credit card type identification, or an on-line input wherein an identification code is typed into a terminal which then sends it to the computer 148 would also be supplied as an input to the computer. An IPIP identification code 173, essentially an electronic serial number which identifies the IPIP 10, the type of medication to be infused thereby and the concentration of the medication is resident in the IPIP 10 and is also telemetered to the computer 148 via the loop antennas 54 and 72. The patient identification input 170 would then be compared to a record in the memory of the computer 148 as to the type of medication which a patient is authorized to receive. If the type of medication read by the code reader 174 and inputted by the medication identification unit 172 is substantially the same as that which the patient is authorized to accept, and if the identification code 173 is verified as being that of the correct patient, the computer will then send a control signal to the valve 154 permitting it to open. If incorrect medication has been placed in the MIU 58, the valve 154 will remain closed and will not open until correct medication is provided, an indication of this error being provided to the operator. Opening a valve 154 puts the medication pump 156 in communication with the medication vial 176. Instead of opening the valve 154, a visual or aural prompt could be provided to signal that the correct medication has been chosen and the medication filling could then be accomplished manually for instance, with the structure illustrated in FIG. 5.

The antechamber 38, in one contemplated embodiment, as in FIG. 6, would be filled with a bactericidal fluid, saline, or other innocuous solution which would provide a buffer between the patient's body and the medication reservoir 30 and would, should the septum 40 fail, cause no harm to the patient. Even if the septum 40 should fail when the antechamber 38 is filled with medication, the volume of the antechamber is sufficiently small so that escape of the small amount of medication disposed therein should not harm the patient.

In one method of filling, according to a prearranged protocol programmed into the memory of the computer 148, the valve 165 would be opened and the suction means 162 would be activated to exhaust the saline within the antechamber 38 through one lumen of the needle 82. As this is being accomplished the valve 158, controlled by the computer 148 would put the other lumen of the hypodermic needle 82 in communication with the pump means 166 so that saline disposed in the fluid reservoir 168 could be pumped into the antechamber 38. This supply of saline and withdrawal of saline would effectively flush the antechamber and is carried out at a pressure such that the ball valve 48 does not open. Of course, other types of flushing could be effected in this general manner. For instance, one lumen could be placed in communication with a supply of saline and the other lumen could be placed in communication with a suction pump. As the suction pump is activated, saline would be drawn into the antechamber and would be evacuated therefrom.

One flushing has been accomplished, the antechamber 38 can then be pressure checked, if desired, by closing of the valve 164 and shutting off of the suction means 162. The pump means 166 would then pump saline into the antechamber 38 pressurizing the antechamber as read out at the pressure transducer 160. This would be at a pressure once again lower than that necessary to open the valve 48. After the pump means 166 pressurizes the antechamber 38 to a preselected pressure, the pump means 166 would shut down. The pressure as measured at transducer 160 would be looked at by the computer 148 over time to see whether or not any decay in pressure was observed. Any decay in pressure would be indicative of a leak somewhere in the antechamber 38. Once the pressure integrity of the antechamber was verified, the valve 158 would be switched to its other position by a control signal from computer 148 such that the medication pump 56 would be put in communication with a lumen of the hypodermic needle 82. Medication could then be pumped from the vial 176, by the medication pump 156, into the antechamber 38. This would be a accomplished at a pressure sufficient to open the ball valve 48 so that the pumped medication could flow into the medication reservoir 26.

As the diaphragm 30 distends and comes in contact with the limit switch 36, a fill switch sensor 178 sends a signal to the loop antenna 54 which is received by the loop antenna 72 which is coupled to the computer 148. Upon receipt of the signal, the computer 148 shuts down the medication pump 156 and filling has been completed. The antechamber 38 can then be flushed as hereinbefore described and the hypodermic needle 82 and electrode needle 84 can be withdrawn.

With reference to FIG. 7 an alternate hypodermic needle 180 is illustrated which may be used instead of hypodermic needle 82. Hypodermic needle 180 is coupled through a valve 182 to a pump means 184 and a suction means 186. By employing this embodiment, saline can be supplied by the pump means 184 into the single lumen of the hypodermic needle 180 and can be sucked therefrom by the suction means 186 if suitable venting means are provided. This embodiment would find particular application for use in conjunction with the antechamber 126 illustrated in FIG. 5, such that this embodiment can be employed to flush not only the antechamber but also the medication reservior used in conjunction therewith.

Under some circumstances it might be desirable to entirely forego the flushing of the reservoir 38 and in such an instance, the suction and pump means of the MIU would be dispensed with and medication would be directly pumped once that the medication code was verified. As an additional feature, depletion of the medication in the vial as it is pumped into the antechamber of the IPIP can be determined by suitable means such as by weighing the contents thereof or by optically detecting the depletion of the contents in the vial.

To prevent contamination of the medication with skin, hair, or other impurities which might enter the medication delivery hypodermic needle as it passes into a patient, a stylet, not illustrated, can be disposed within the needle and can be removed therefrom to block the exit hole thereof. When the needle is properly positioned the stylet can be withdrawn. To further control contamination a bactericidal agent can be supplied to the antechamber or the reservoir or both or such an agent can be placed directly inthe medication to be delivered. Furthermore, as previously noted the torroidal filters disposed in the antechambers are preferably of sufficiently small pore size so as to preclude the passage of bacteria from the antechambers to their associated medication reservoirs.

Since the medication reservoirs of all the embodiments of the present invention and the antechambers associated therewith are under negative pressure relative to the pressure of the body, if a leak occurs body fluids would enter the IPIP due to this pressure differential rather than permitting medication to leak therefrom into the body of the patient. However, as long as the medication reservoirs are not at a pressure significantly higher than ambient pressure, there will not be a significantly high rate of inadvertant medication flow into the patient's body. As an additional safety feature, the medication reservoirs are of a sufficiently small size such that their volume for any given medication is less than that which could contain a lethal dose of the given medication. For example, if the IPIP is employed to infuse insulin, the antechamber thereof would be sized to hold less than 100 units of insulin, an amount considered to be lethal.

It will be understood that various changes in the details, materials, arrangements of parts and operational conditions which have been herein described and illustrated in order to explain the nature of the invention may be made by those skilled in the art within the principles and scope of the present invention.

Having thus set forth the nature of the invention, what is claimed is:

1. A system having a medication infusion apparatus including a medication container and an apparatus for filling the medication container, said system comprising in combination:

a medication container having an input;

a dispensing means adapted to communicate with said input of said medication container; and, a valve, operably disposed at said input of said medication container, said valve comprising a reciprocally mounted valve poppet which is urged into an open position when a portion of said dispensing means is disposed in a preselected position in said medication infusion apparatus, removal of said portion of said dispensing means from said preselected position causing said valve poppet to be urged into a closed position, said dispensing means in fluid communication with said medication container only when said valve poppet is urged into said open position.

2. A combination in accordance with claim 1, further comprising flushing means operably coupled to said dispensing means for flushing at least a portion of said medication container.

3. A combination in accordance with claim 2, wherein said flushing means comprises means for supplying and means for evacuating a flushing fluid from said medication container.

4. A combination in accordance with claim 3, wherein said dispensing means comprises a hypodermic needle, said supply means and evacuation means being connectable thereto.

5. A combination in accordance with claim 4, wherein said hypodermic needle comprises two lumens, one of said lumens being connectable to said supply means, the other of said lumens being connectable simultaneously to said evacuation means.

6. A combination in accordance with claim 2, wherein said dispensing means comprising a hypodermic needle having a delivery opening therein, said dispensing means further comprising a stylet for removable selective insertion in said hypodermic needle to block said delivery opening.

7. A combination in accordance with claim 1, further comprising a housing having associated therewith said medication container and means for guiding the position of said dispensing means, said guiding means comprising a control head for accommodating a portion of said dispensing means therethrough, said control head and said housing having complementary structure to aid in alignment when said dispensing means is operably disposed relative to said input of said medication container.

8. A combination in accordance with claim 1, further comprising means for checking at least a portion of said medication container for leaks.

9. A combination in accordance with claim 8, wherein said checking means comprises:
pressurized injection means for injecting a fluid into said portion of said medication container;
means for measuring the pressure within said portion of said medication container over a period of time after said injecting of said fluid, decay of the measured pressure over said period of time being indicative of a leak; and
means for evacuating said fluid from said portion of said medication container.

10. A combination in accordance with claim 9, wherein said medication container comprises an antechamber and a reservoir, said valve being disposed therebetween for permitting the flow of fluid from said antechamber to said reservoir, said at least a portion of said medication container comprising said antechamber, a portion of said pressurized injection means positioned in said antechamber but not disposed in said preselected position, so that said valve poppet remains closed to permit checking said antechamber for leaks.

11. A combination in accordance with claim 9, wherein said medication container comprises an antechamber and a reservoir, said valve being disposed between said antechamber and said reservoir, a portion of said pressurized injection means being insertable into said antechamber, such insertion opening said valve to permit checking of said reservoir and said antechamber for leaks.

12. A combination in accordance with claim 1, wherein said means for dispensing medication into said medication container has associated therewith a supply of medication, said medication container being at a lower pressure than said supply of medication, the pressure differential therebetween thereby causing the movement of said medication from said medication supply to said medication container.

13. A combination in accordance with claim 12, wherein said medication container comprises an antechamber and a reservoir, said valve being disposed between said antechamber and said reservoir, a portion of said dispensing means being insertable into said antechamber, such insertion opening said valve to permit filling of said reservoir.

14. A combination in accordance with claim 12, wherein said medication container is at a pressure lower than ambient pressure.

15. A combination in accordance with claim 1, further comprising means for detecting and indicating if said filling apparatus is in communication with a predetermined type of medication.

16. A combination in accordance with claim 15, wherein said detecting means comprises
means for inputting a patient code,
means for inputting a medication code, and
means for comparing said codes.

17. A combination in accordance with claim 16, further comprising means for identifying the particular medication infusion apparatus to be filled.

18. A combination in accordance with claim 17, wherein said identifying means comprises an electronically identifiable code disposed in said medication infusion apparatus, said comparing means further comparing said electronically identifiable code to said patient code and said medication code.

19. A combination in accordance with claim 17, wherein said means for inputting a medication code comprises an optically readable bar code.

20. A medication infusion apparatus having a medication container and an apparatus for filling the medication container comprising in combination:
a medication container maintained at a pressure below ambient pressure, said medication container having an input;
a dispensing means adapted to communicate with said input of said medication container, and;
a valve means, operably disposed at said input of said medication container, said valve means being opened mechanically through placement of a portion of said dispensing means in a preselected position.

21. A combination in accordance with claim 20, wherein said valve means comprises a reciprocally mounted valve poppet which is urged into an open position when said portion of said dispensing means is disposed in said preselected position, removal of said portion of said dispensing means from said preselected position causing said valve poppet to be urged into a closed position.

22. A combination in accordance with claim 20, wherein said dispensing means has associated therewith a supply of medication, said container being at a lower pressure than said supply of medication, the pressure differential therebetween thereby causing the movement of said medication from said medication supply into said medication container only when said valve means is urged into an open position.

23. A combination in accordance with claim 22, further comprising flushing means operably coupled to said dispensing means for flushing at least a portion of said medication container.

24. A combination in accordance with claim 23, wherein said flushing means comprises means for supplying and means for evacuating a flushing fluid from said medication container.

25. A combination in accordance with claim 24, wherein said dispensing means comprises a hypodermic needle, said supply means and evacuation means being connectable thereto.

26. A combination in accordance with claim 25, wherein said hypodermic needle comprises two lumens, one of said lumens being connectable to said supply means, the other of said lumens being connectable simultaneously to said evacuation means.

27. A combination in accordance with claim 22, wherein said input of said medication container comprises an antechamber, said apparatus comprising a housing having associated therewith said medication container, said housing having a tapered entry port with the wide portion thereof opening through said housing, the narrower portion of said entry port being located adjacent to the entrance of said antechamber, said tapered entry port for guiding the entry of said portion of said dispensing means into said antechamber.

28. A combination in accordance with claim 27, wherein said tapered entry port is substantially conical in shape.

29. A combination in accordance with claim 28, wherein the tapered surface of said entry port is relatively smooth and hard.

30. A combination in accordance with claim 22, further comprising means for checking at least a portion of said medication container for leaks.

31. A combination in accordance with claim 30, wherein said checking means comprises:
pressurized injection means for injecting a fluid into said portion of said medication container;
means for measuring the pressure within said portion of said medication container over a period of time after said injecting of said fluid, decay of the measured pressure over said period of time being indicative of a leak; and
means for evacuating said fluid from said portion of said medication container.

32. A combination in accordance with claim 31, wherein said medication container comprises an antechamber and a reservoir, said valve means being disposed between said antechamber and said reservoir, a portion of said pressurized injection means being insertable into said antechamber, such insertion causing said injection means to be in fluid communication with said reservoir thereby permitting checking of said reservoir and said antechamber for leaks.

33. A combination in accordance with claim 22, wherein said medication container comprises an antechamber and a reservoir, said valve means being disposed between said antechamber and said reservoir, a portion of said dispensing means being insertable into said antechamber, such insertion opening said valve to permit filling of said reservoir.

34. A combination in accordance with claim 22, wherein said medication container comprises an antechamber and a reservoir, said valve being disposed therebetween for selectively isolating said antechamber from said reservoir, the volume of said antechamber when isolated from said reservoir being of a magnitude selected so that said antechamber cannot contain a lethal dose of a given medication selected to be infused by said medication infusion apparatus.

35. A combination in accordance with claim 22, wherein said medication container comprises an antechamber and a reservoir.

36. A combination in accordance with claim 35, wherein said valve means is disposed between said antechamber and said reservoir for selectively isolating said antechamber from said reservoir, and wherein said antechamber further comprises a self-sealing septum for allowing insertion by said dispensing means.

37. A combination in accordance with claim 36, further comprising filter means for filtering fluid communicated between said antechamber and said reservoir.

38. A combination in accordance with claim 37 wherein said filter means comprises a filter having a pore size selected to preclude passage of bacteria there through.

39. A combination in accordance with claim 38, wherein said pore size is less than or equal to 2 microns.

40. The apparatus of claim 22, wherein said dispensing means comprises a hypodermic needle in fluid communication with a supply of medication maintained at a pressure equal to or less than ambient pressure so that medication will not be drawn from said dispensing means when said needle is injected into a patient's body, unless said hollow needle is disposed in said preselected position in said medication infusion apparatus.

41. The apparatus of claim 22, wherein said dispensing means comprises a hypodermic needle in fluid communication with a vial containing said supply of medication, and wherein medication is drawn through said hypodermic needle and into medication container only when said hypodermic needle is disposed in said preselected position.

42. A medication infusion apparatus having a medication reservoir, adapted to be filled by means of a hypodermic needle in fluid communication with a medication source, said medication infusion apparatus comprising:
a reservoir for storing selected medication maintained at a pressure lower than both ambient pressure and the pressure of said medication source;
an antechamber with at least a portion of one wall comprising a self-sealing septum, said antechamber being in fluid communication with said reservoir, said hypodermic needle adapted to be inserted through said self-sealing septum into said antechamber;
a valve means being disposed in said antechamber, said valve means adapted to be opened mechanically through placement of a portion of said hypodermic needle in a selected position, wherein said reservoir is in fluid communication with said antechamber only when said valve means is open, thereby causing movement of medication from said medication source into said reservoir due to the pressure differential between said medication source and said reservoir.

43. The apparatus of claim 42, wherein said valve means comprises a reciprocally mounted valve poppet which is adapted to be urged into an open position when said portion of said hypodermic needle is disposed in said preselected position, removal of said portion of said hypodermic needle from said preselected position causing said valve poppet to be urged into a closed position.

44. The apparatus of claim 43, wherein said valve poppet includes a valve seat surrounding a recess and said valve means further comprises a biasing means secured within said antechamber for holding said valve seat in sealing contact with said septum, until such time as said hypodermic needle presses against said recess bottom urging said poppet valve into an open position.

45. The apparatus of claim 42, wherein said antechamber further comprises an annular fluid manifold allowing fluid communication from said antechamber to said reservoir.

46. The apparatus of claim 45, wherein said annular fluid manifold further includes an annular filter means therein for filtering fluid communicated between said antechamber and said reservoir.

47. The apparatus of claim 42, wherein said medication infusion apparatus further comprises a filter means for filtering fluid communicated between said antechamber and said reservoir.

48. The apparatus of claim 42, further comprising a housing, said housing having a tapered entry port with the wide portion thereof opening through said housing, the narrower portion of said entry port being located adjacent to the entrance of said antechamber, said tapered entry port for guiding the entry of said hypodermic needle into said antechamber.

49. The apparatus of claim 48, wherein said tapered entry port is substantially conical in shape.

50. The apparatus of claim 42, wherein said reservoir includes:
a medication chamber for storing said selected medication having an expandable base portion for altering the volume of said medication chamber; and,
a vapor chamber located adjacent to said medication chamber, wherein said expandable base portion is a common wall to said medication chamber and said vapor chamber, and wherein said vapor chamber has therein a fluid having a vapor pressure less than ambient pressure when said fluid is at the temperature of a living body.

51. A medication infusion apparatus adapted to be filled by a dispensing means, said medication infusion apparatus comprising:
a medication container having an input; and,
a valve, operably disposed at said input of said medication container, said valve comprising a reciprocally mounted valve poppet adapted to be urged into an open position when a portion of said dispensing means is disposed in a preselected position in said medication infusion apparatus.

52. A combination in accordance with claim 51, wherein said input of said medication container comprises an antechamber, said apparatus comprising a housing having associated therewith said medication container, said housing having a tapered entry port with the wide portion thereof opening through said housing, the narrower portion of said entry port being located adjacent to the entrance of said portion of said dispensing means into said antechamber.

53. A combination in accordance with claim 52 wherein said tapered entry port is substantially conical in shape.

54. A combination in accordance with claim 52, wherein the tapered surface of said entry port is relatively smooth and hard.

55. A combination in accordance with claim 51, further comprising means responsive to the filling of said medication container for indicating when said medication container has disposed therein a preselected quantity of medication.

56. A combination in accordance with claim 55, wherein a portion of said medication container expands in proportion to the quantity of medication disposed therein, said responsive means comprising a switch which is tripped upon said expansion of said portion of said medication container.

57. A combination in accordance with claim 56, wherein said means responsive to the filling of said medication container further comprises signal means, the tripping of said switch activating said signal means.

58. A combination in accordance with claim 57, wherein said means responsive to the filling of said medication container further comprises means for telemetering the signal produced by said signal means; receiving means for receiving said signal; and indicating means for indicating when said signal is received by said receiver means, said indicating means being coupled to said receiving means.

59. A combination in accordance with claim 51, wherein said medication container comprises an antechamber and a reservoir, said valve being disposed therebetween for selectively isolating said antechamber from said reservoir, the volume of said antechamber when isolated from said reservoir being of a magnitude selected so that said antechamber cannot contain a lethal dose of a given medication selected to be infused by said medication infusion apparatus.

60. A combination in accordance with claim 51, wherein said medication container comprises an antechamber and a reservoir.

61. A combination in accordance with claim 60, wherein said valve disposed between said antechamber and said reservoir selectively isolates said antechamber from said reservoir.

62. A combination in accordance with claim 60, further comprising filter means for filtering fluid communicated between said antechamber and said reservoir.

63. A combination in accordance with claim 62, wherein said filter means comprises a filter having a pore size selected to preclude passage of bacteria therethrough.

64. A combination in accordance with claim 63, wherein said pore size is less than or equal to 2 microns.

* * * * *